US010324050B2

(12) United States Patent
Hench et al.

(10) Patent No.: US 10,324,050 B2
(45) Date of Patent: Jun. 18, 2019

(54) MEASUREMENT SYSTEM OPTIMIZATION FOR X-RAY BASED METROLOGY

(71) Applicant: KLA-Tencor Corporation, Milpitas, CA (US)

(72) Inventors: John J. Hench, Los Gatos, CA (US); Andrei V. Shchegrov, Campbell, CA (US); Michael S. Bakeman, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 198 days.

(21) Appl. No.: 14/994,817

(22) Filed: Jan. 13, 2016

(65) Prior Publication Data
US 2016/0202193 A1    Jul. 14, 2016

Related U.S. Application Data

(60) Provisional application No. 62/103,428, filed on Jan. 14, 2015.

(51) Int. Cl.
*G01N 23/20008* (2018.01)

(52) U.S. Cl.
CPC .............................. *G01N 23/20008* (2013.01)

(58) Field of Classification Search
CPC .................................................. G01N 23/20008
USPC ............................................ 702/85, 189, 31
See application file for complete search history.

(56) References Cited

U.S. PATENT DOCUMENTS

| 5,608,526 | A |   | 3/1997 | Piwonka-Corle et al. |
| 5,811,835 | A | * | 9/1998 | Seiki ................. H01L 29/42384 257/57 |
| 5,859,424 | A |   | 1/1999 | Norton et al. |
| 6,429,943 | B1 |  | 8/2002 | Opsal et al. |

(Continued)

FOREIGN PATENT DOCUMENTS

WO    WO2005119169 A2    12/2005

OTHER PUBLICATIONS

International Search Report dated Apr. 29, 2016, for PCT Application No. PCT/US2016/013467 filed on Jan. 14, 2016 by KLA-Tencor Corporation, 3 pages.

*Primary Examiner* — Mohammed Shamsuzzaman
(74) *Attorney, Agent, or Firm* — Spano Law Group; Joseph S. Spano

(57) ABSTRACT

Methods and systems for optimizing measurement system parameter settings of an x-ray based metrology system are presented. X-ray based metrology systems employing an optimized set of measurement system parameters are used to measure structural, material, and process characteristics associated with different semiconductor fabrication processes with greater precision and accuracy. In one aspect, a set of values of one or more machine parameters that specify a measurement scenario is refined based at least in part on a sensitivity of measurement data to a previous set of values of the one or more machine parameters. The refinement of the values of the machine parameters is performed to maximize precision, maximize accuracy, minimize correlation between parameters of interest, or any combination thereof. Refinement of the machine parameter values that specify a measurement scenario can be used to optimize the measurement recipe to reduce measurement time and increase measurement precision and accuracy.

20 Claims, 2 Drawing Sheets

(56) References Cited

U.S. PATENT DOCUMENTS

| | | | |
|---|---|---|---|
| 6,633,831 | B2 | 10/2003 | Nikoonahad et al. |
| 6,734,967 | B1 | 5/2004 | Piwonka-Corle et al. |
| 6,816,570 | B2 | 10/2004 | Janik et al. |
| 6,895,075 | B2 | 5/2005 | Yokhin et al. |
| 6,972,852 | B2 | 12/2005 | Opsal et al. |
| 7,450,225 | B1 | 11/2008 | Liu et al. |
| 7,478,019 | B2 | 1/2009 | Zangooie et al. |
| 7,481,579 | B2 * | 1/2009 | Yokhin ............... G03F 7/70633 378/205 |
| 7,511,265 | B2 * | 3/2009 | Walsh ................. G01N 21/274 250/252.1 |
| 7,653,174 | B2 * | 1/2010 | Mazor ................. G01N 23/223 378/50 |
| 7,698,098 | B2 | 4/2010 | Ritter et al. |
| 7,804,059 | B2 * | 9/2010 | Harrison ............. G01N 21/274 250/252.1 |
| 7,826,071 | B2 | 11/2010 | Shchegrov et al. |
| 7,921,383 | B1 | 4/2011 | Wei |
| 7,929,667 | B1 | 4/2011 | Zhuang et al. |
| 7,933,026 | B2 | 4/2011 | Opsal et al. |
| 7,973,930 | B2 * | 7/2011 | Tanaka ................ G01N 21/211 356/364 |
| 8,153,987 | B2 * | 4/2012 | Hurst .................. G01N 21/278 250/252.1 |
| 8,289,527 | B2 | 10/2012 | Li et al. |
| 8,296,687 | B2 | 10/2012 | Mitrovic et al. |
| 8,687,766 | B2 * | 4/2014 | Wormington ........ G01N 23/207 378/70 |
| 9,466,726 | B2 * | 10/2016 | Yamazaki .......... H01L 29/41733 |
| 2001/0000620 | A1 * | 5/2001 | Ishida .................. H01L 21/268 257/59 |
| 2003/0187604 | A1 | 10/2003 | Drege et al. |
| 2004/0004220 | A1 * | 1/2004 | Suzuki ............. H01L 29/42384 257/66 |
| 2004/0218717 | A1 * | 11/2004 | Koppel .................. G01N 23/20 378/70 |
| 2005/0184233 | A1 * | 8/2005 | Park ..................... G01N 23/083 250/307 |
| 2008/0049214 | A1 | 2/2008 | Maznev et al. |
| 2009/0157343 | A1 * | 6/2009 | Kaushal ............... G01B 21/045 702/97 |
| 2009/0319196 | A1 * | 12/2009 | Schaller ................ G01N 21/84 702/31 |
| 2012/0323356 | A1 * | 12/2012 | Dziura .................. G01N 21/47 700/121 |
| 2013/0114085 | A1 | 5/2013 | Wang et al. |
| 2013/0132021 | A1 * | 5/2013 | Kwak .................. G01N 21/274 702/104 |
| 2013/0304424 | A1 * | 11/2013 | Bakeman ............. G03F 7/70625 702/189 |
| 2014/0019097 | A1 * | 1/2014 | Bakeman ............. G06F 17/5068 703/1 |
| 2014/0111791 | A1 | 4/2014 | Manassen et al. |
| 2014/0172394 | A1 | 6/2014 | Kuznetsov et al. |
| 2014/0222380 | A1 | 8/2014 | Kuznetsov et al. |
| 2014/0297211 | A1 | 10/2014 | Pandev et al. |
| 2014/0316730 | A1 | 10/2014 | Shchegrov et al. |
| 2015/0042984 | A1 | 2/2015 | Pandev et al. |
| 2015/0046118 | A1 | 2/2015 | Pandev et al. |

* cited by examiner

MEASUREMENT SYSTEM OPTIMIZATION FOR X-RAY BASED METROLOGY

CROSS REFERENCE TO RELATED APPLICATION

The present application for patent claims priority under 35 U.S.C. § 119 from U.S. provisional patent application Ser. No. 62/103,428, entitled "Optimization of the X-Ray Scattering Measurement Setup for Maximizing the Metrological Precision for Target Structures of Interest to the Semiconductor Industry," filed Jan. 14, 2015, the subject matter of which is incorporated herein by reference in its entirety.

TECHNICAL FIELD

The described embodiments relate to x-ray based metrology systems and methods, and more particularly to methods and systems for improved measurement of structural, material, and process parameters.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. A number of optical metrology based techniques including scatterometry and reflectometry implementations and associated analysis algorithms are commonly used to characterize critical dimensions, film thicknesses, composition and other parameters of nanoscale structures.

Traditionally, scatterometry measurements are performed on targets consisting of thin films and/or repeated periodic structures. During device fabrication, these films and periodic structures typically represent the actual device geometry and material structure, or an intermediate design. As devices (e.g., logic and memory devices) move toward smaller nanometer-scale dimensions, characterization becomes more difficult. Devices incorporating complex three-dimensional geometry and materials with diverse physical properties contribute to characterization difficulty. For example, modern memory structures are often high-aspect ratio, three-dimensional structures that make it difficult for optical radiation to penetrate to the bottom layers. In addition, the increasing number of parameters required to characterize complex structures (e.g., FinFETs), leads to increasing parameter correlation. As a result, the parameters characterizing the target often cannot be reliably decoupled with available measurements. In another example, opaque, high-k materials are increasingly employed in modern semiconductor structures. Optical radiation is often unable to penetrate layers constructed of these materials. As a result, measurements with thin-film scatterometry tools such as ellipsometers or reflectometers are becoming increasingly challenging.

In response to these challenges, more complex optical tools have been developed. For example, tools with multiple angles of illumination, shorter and broader ranges of illumination wavelengths, and more complete information acquisition from reflected signals (e.g., measuring multiple Mueller matrix elements in addition to the more conventional reflectivity or ellipsometric signals) have been developed. However, these approaches have not reliably overcome fundamental challenges associated with measurement of many advanced targets (e.g., complex 3D structures, structures smaller than 10 nm, structures employing opaque materials) and measurement applications (e.g., line edge roughness and line width roughness measurements).

Another response to these recent challenges in semiconductor manufacturing has been the adoption of x-ray metrology for measurements including film thickness, composition, strain, surface roughness, line edge roughness, and porosity.

In some examples, traditional x-ray based metrology tools lack the ability to adapt to a wide range of measurement system configurations. This limits the ability to select a measurement system configuration tuned for a specific metrology application. In some of these examples, the lack of machine flexibility and machine parameter optimization results in a measurement system that is unable to resolve particular parameters of interest. In other examples, a measurement system is unable to achieve the required measurement precision for particular parameters of interest in a reasonable amount of measurement time.

In some other examples, x-ray metrology tools include a broader range of measurement system configurations. However, the use of the complete range of available system parameter values may result in excessively long measurement times. In one example, X-ray scattering measurements are performed on periodic targets. Typically, the intensity of the X-ray diffraction orders is detected at a set of evenly spaced angles orthogonal to the direction of periodicity. Such spacing may be too coarse and the measurement system is unable to resolve the particular parameters of interest. Alternatively, a closer spacing may be employed, but the measurement system is unable to achieve the required measurement precision in a reasonable amount of measurement time.

Future X-ray based metrology applications present challenges due to increasingly small resolution requirements, multi-parameter correlation, increasingly complex geometric structures, and increasing use of opaque materials. Thus, methods and systems for improved selection of X-ray based metrology system parameters are desired.

SUMMARY

Methods and systems for optimizing measurement system parameter settings of an x-ray based metrology system are presented. X-ray based metrology systems employing an optimized set of measurement system parameters are used to measure structural, material, and process characteristics associated with different semiconductor fabrication processes with greater precision and accuracy.

In one aspect, a set of values of one or more machine parameters that specify a measurement scenario is refined based at least in part on a sensitivity of measurement data to a previous set of values of the one or more machine parameters. The refinement of the values of the machine parameters is performed to maximize precision, maximize accuracy, minimize correlation between parameters of interest, or any combination thereof. Refinement of the machine parameter values that specify a measurement scenario can be used to optimize the measurement recipe to reduce measurement time and increase measurement precision and accuracy. In addition, computation time for library generation, regression, and analysis is also reduced. In some examples, accuracy, precision, and model stability are improved within the constrained measurement space that corresponds to the selected machine parameter values.

In some examples, the refinement of the set of machine parameter values involves determining a measurement model of the measured target structures. The measurement model relates values of one or more parameters of interest and the previous set of values of the one or more machine parameters to an amount of x-ray measurement data. In some examples, the refined set of values of the one or more machine parameters is determined based on an optimization that involves a minimization of a variance or covariance of the values of the one or more parameters of interest subject to a constraint, for example, on measurement duration. In some other examples, the second set of values of the one or more machine parameters is determined based on an optimization that involves a minimization of measurement duration subject to a constraint, for example, on a variance or covariance of the values of the one or more parameters of interest.

In a further aspect, the refined set of machine parameter values is employed in subsequent set of measurements. The resulting measurement data is analyzed again to further optimize the set of values of the machine parameters. In this manner, the refinement of the set of values of the machine parameters is iterated until a desired measurement precision is achieved.

In another further aspect, the refinement of a set of values of one or more machine parameters involves determining a model that relates values of the one or more machine parameters to the measurement data. A refined set of machine parameter values is determined such that one or more signals of subsequently collected measurement data converges toward a minimum or maximum value. In this manner, changes to values of the machine parameters are driven by values of measured data in an iterative, feedback approach. In general, the signals indicative of the refined set of machine parameter values takes into account the stochastics or statistical properties of the measurement process. In some embodiments, the refinement of the set of machine parameter values is determined by a Kalman filter, Extended Kalman Filter, or any related statistical filter such as a Bayesian or particle filter.

In a further aspect, measurement data associated with measurements of one or more target structures is simulated. In some examples, a number of simulations of a measurement model, including expected variations in the values of parameters of interest and a noise model, provide measurement data for initialization or refinement of a set of machine parameter values. In one example, measurements of an ensemble of shapes sampled from its expected range are simulated. Additionally, a large set of measurement sensitivities for machine parameters are computed for each model. A Monte Carlo based algorithm is employed to subsample the set of possible measurement parameters and select the sample which optimizes an appropriate measure of the desired measurement precision.

In another further aspect, the results of a measurement analysis are compared with reference measurement results to determine if a difference between the estimated parameter values and the parameter values derived from the reference measurement is within a predetermined threshold. If so, an optimized measurement recipe based on the refined set of machine parameter values is achieved. If not, the optimization of the set of machine parameter values is iterated until an optimized measurement recipe is achieved.

In general, any number of machine parameters may be refined to improve measurement precision. Machine parameters subject to refinement in accordance with the methods and systems described herein, include, but are not limited to an angle of incidence, an azimuth angle, a beam photon energy, a measurement duration, a beam divergence, an illumination spot size, and a detector location.

In another further aspect, multiple targets are employed as part of a refinement of the measurement recipe. When multiple targets are employed certain parameters may be floated together and others separately.

In another further aspect, the values of a parameter of interest are constrained or parameterized as part of a refinement of the measurement recipe.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Figure 1:
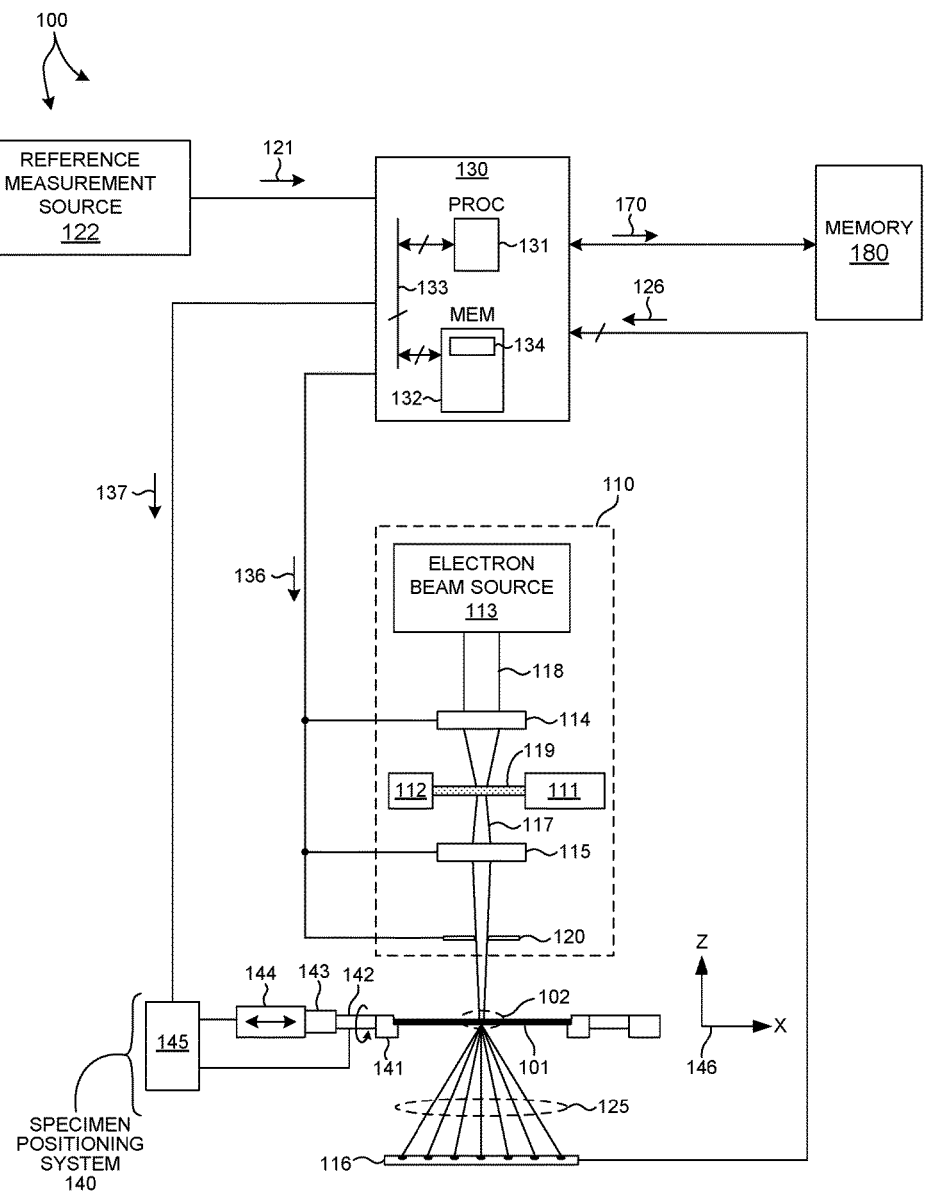
FIG. 1 is a diagram illustrative of a metrology system 100 configured to optimize a measurement recipe based on refinement of machine parameter values that specify a measurement scenario in accordance with the methods described herein.

Reference will now be made in detail to background examples and some embodiments of the invention, examples of which are illustrated in the accompanying drawings.

Methods and systems for optimizing measurement system parameter settings of an x-ray based metrology system are presented. X-ray based metrology systems employing an optimized set of measurement system parameters are used to measure structural (e.g., dimensional characteristics of structures and films, etc.), material (e.g., material composition), and process characteristics (e.g., lithography focus and dosage) associated with different semiconductor fabrication processes with greater precision and accuracy.

In general, x-ray metrology techniques discussed herein (e.g., metrology based on x-ray diffraction and x-ray scattering) are indirect methods of measuring physical properties of a specimen under inspection. In most cases, the measured values cannot be used to directly determine the physical properties of the specimen. The nominal measurement process consists of parameterization of the structure (e.g., film thicknesses, critical dimensions, shape parameters, overlay, etc.) and the machine (e.g., angles of incidence, azimuth angle, beam energy, etc.). A measurement model is created that attempts to predict the measured values. The model includes parameters associated with the machine ($P_{machine}$) and the specimen ($P_{specimen}$).

Machine parameters are parameters used to characterize the metrology tool itself. Exemplary machine parameters of an x-ray metrology system include angle of incidence (AOI), azimuth angle ($A_z$), beam energy (I), measurement duration ($\tau$), beam divergence ($\alpha$), illumination spot size, detector location, etc. Specimen parameters are parameters used to characterize the specimen. For a thin film specimen, exemplary specimen parameters include refractive index, dielectric function tensor, nominal layer thickness of all layers, layer sequence, etc.

For measurement purposes, the machine parameters are treated as known parameters and the specimen parameters of interest (e.g., a subset of specimen parameters) are treated as unknown, floating parameters. The floating parameters are resolved by an iterative process (e.g., regression, library matching, etc.) that produces the best fit between theoretical predictions and experimental data. The unknown specimen parameters, $P_{specimen}$, are varied and the model output values are calculated until a set of specimen parameter values are determined that results in a close match between the model output values and the experimentally measured values.

The machine parameter settings for a particular measurement application influence the achievable measurement precision and accuracy. Measurement precision refers to the repeatability of the measurement. Measurement accuracy refers to the ability of the measurement tool to track the results of an absolute reference measurement, or track measurement values that are known a priori (e.g. programmed variations for the parameters of interest).

In general, more precise measurements of a parameter of interest can be made by increasing the differential sensitivity of the measured data (e.g., intensity, spectra, etc.) to changes in value of the parameter of interest, selecting signals with lower levels of random noise, or a combination of both. For many parameters of interest in semiconductor manufacturing, the measurement precision for a particular parameter of interest is related both to the absolute sensitivity of the measurement to changes in value of the parameter of interest and sensitivity of the measurement to changes in value of other parameters (i.e., correlation of the measurement with other parameters). In addition, the noise level of the measured signals also limits the achievable measurement precision.

In one example, differential sensitivity is increased by reducing the total number of parameters floated in the optimization program employed to estimate the parameters of interest. However, in practice, there are limits to the reduction of the total number of floated parameters. For example, the selection of floating parameters is determined by evaluating the sensitivity of the measurement model to variation of each parameter. In some examples, fixed error analysis is performed to determine a suitable set of parameters to float. However, in many cases, the specimen parameters are highly correlated. This can lead to instability in the estimation of the parameter. In some cases, this is resolved by fixing certain specimen parameters. However, this often results in significant errors in the estimation of the remaining parameters.

In another example, differential sensitivity is increased by utilizing as many independent measurements as possible in the parameter estimation. However, this approach also has practical limits. In many cases, the high degree of correlation among the model parameters calls for the use of broad ranges of machine parameters, and even under these conditions, the models may fail. Even if measurement recipes employing multiple measurements over a broad range of machine parameters lead to satisfactory measurement results, the cost in terms of throughput time may be undesirable.

In one aspect, a set of values of one or more machine parameters that specify a measurement scenario is refined based at least in part on a sensitivity of measurement data associated with measurements of target structure by an x-ray based metrology system on a previous set of values of the one or more machine parameters. The refinement of the values of the machine parameters is performed to maximize precision, maximize accuracy, minimize correlation between parameters of interest, or any combination thereof. Refinement of the machine parameter values that specify a measurement scenario can be used to optimize the measurement recipe to reduce measurement time and increase measurement precision and accuracy. In addition, computation time for library generation, regression, and analysis is also reduced. In some examples, accuracy, precision, and model stability are improved within the constrained measurement space that corresponds to the selected machine parameter values.

FIG. 1 illustrates a system 100 for measuring characteristics of a specimen in accordance with the exemplary methods presented herein. In the embodiment depicted in FIG. 1, computing system 130 is configured as a measurement recipe engine configured to implement measurement recipe building and analysis functionality as described herein. As shown in FIG. 1, the system 100 may be used to perform small angle x-ray scatterometry (SAXS) measurements over an inspection area 102 of a specimen 101 disposed on a specimen positioning system 140. In some embodiments, the inspection area 102 has a spot size of fifty micrometers or less.

In the depicted embodiment, metrology tool 100 includes a liquid metal based x-ray illumination system 110 and an x-ray detector 116. X-ray illumination system 110 includes a high-brightness, liquid metal x-ray illumination source. A jet of liquid metal 119 is produced from a liquid metal container 111 and collected in a liquid metal collector 112. A liquid metal circulation system (not shown) returns liquid metal collected by collector 112 to liquid metal container 111. The jet of liquid metal 119 includes one or more elements. By way of non-limiting example, the jet of liquid metal 119 includes any of Aluminum, Zinc, Gallium, Indium, Tin, Thallium, and Bismuth. In this manner, the jet of liquid metal 119 produces x-ray lines corresponding with its constituent elements. In some embodiments, the x-ray illumination system 110 is configured to generate wavelengths between 0.01 nanometers and 1 nanometer. Exemplary methods and systems for generating high brightness, liquid metal x-ray illumination are described in U.S. Pat. No. 7,929,667, issued on Apr. 19, 2011, to KLA-Tencor Corp., the entirety of which is incorporated herein by reference.

An electron beam source 113 (e.g., electron gun) produces a stream of electrons 118 that is directed by electron optics 114 to the jet of liquid metal 119. Suitable electron optics 114 includes electromagnets, permanent magnets, or a combination of electromagnets and permanent magnets for focusing the electron beam and directing the beam at the liquid metal jet. The coincidence of the jet of liquid metal 119 and the stream of electrons 118 produces an x-ray beam 117 incident on inspection area 102 of specimen 101. X-ray optics 115 shape and direct incident x-ray beam 117 to specimen 101. In some examples, x-ray optics 115 monochromatize the x-ray beam that is incident on the specimen 101. In some examples, x-ray optics 115 collimate or focus the x-ray beam 117 onto inspection area 102 of specimen 101. In some embodiments, x-ray optics 115 includes one or more x-ray collimating mirrors, x-ray apertures, x-ray monochromators, and x-ray beam stops, multilayer optics, refractive optics, diffractive optics such as zone plates, or any combination thereof.

X-ray detector 116 collects x-ray radiation 125 scattered from specimen 101 and generates an output signal 126 indicative of properties of specimen 101 that are sensitive to the incident x-ray radiation. Scattered x-rays 125 are collected by x-ray detector 116 while specimen positioning system 140 locates and orients specimen 101 to scatter x-rays that are variably oriented relative to the sample. The x-ray detector 116 is able to resolve one or more x-ray photon energies and produces signals for each x-ray energy component indicative of properties of the specimen. In some embodiments, the x-ray detector 116 includes any of a CCD array, a microchannel plate, a photodiode array, a microstrip proportional counter, a gas filled proportional counter, and a scintillator.

Metrology tool 100 also includes a computing system 130 employed to acquire signals 126 generated by x-ray detector 116, and determine properties of the specimen based at least in part on the acquired signals. As illustrated in FIG. 1, computing system 130 is communicatively coupled to x-ray detector 116.

In one example, x-ray detector 116 is an x-ray spectrometer and measurement data 126 includes an indication of the measured spectral response of the specimen based on one or more sampling processes implemented by the x-ray spectrometer.

In a further embodiment, computing system 130 is configured to access model parameters in real-time, employing Real Time Critical Dimensioning (RTCD), or it may access libraries of pre-computed models for determining a value of at least one specimen parameter value associated with the specimen 101. In one example, some form of CD-engine may be used to evaluate the difference between assigned CD parameters of a specimen and CD parameters associated with the measured specimen. Exemplary methods and systems for computing specimen parameter values are described in U.S. Pat. No. 7,826,071, issued on Nov. 2, 2010, to KLA-Tencor Corp., the entirety of which is incorporated herein by reference.

In a further aspect, metrology tool 100 includes a computing system (e.g., computing system 130) configured to implement beam control functionality as described herein. In the embodiment depicted in FIG. 1, computing system 130 is configured as a beam controller operable to control the positioning and spot size of the incident x-ray beam 117 at the desired inspection area 102 of the specimen 101 at any point in time.

As illustrated in FIG. 1, computing system 130 is configured to receive measurement data 126 from x-ray detector 116. In one example, measurement data 126 includes an indication of the measured x-ray response of the specimen. Based on the distribution of the measured x-ray response on the surface of detector 116, the location and area of incidence x-ray beam 117 on specimen 101 is determined by beam controller 130. In one example, pattern recognition techniques are applied by computing system 130 to determine the location and area of incidence of x-ray beam 117 on specimen 101 based on measurement data 126. In response computing system 130 generates a command signal 136 communicated to any of electron optics 114, x-ray optics 115, and x-ray illumination slit 120 to redirect and reshape incident x-ray beam 117 such that incident x-ray beam 117 illuminates the desired inspection area 102 of specimen 101.

In another aspect, SAXS measurements of a particular inspection area are performed at a number of different out of plane orientations (e.g., angles of incidence and azimuth angles). This increases the precision and accuracy of measured parameters and reduces correlations among parameters by extending the number and diversity of data sets available for analysis to include a variety of large-angle, out of plane orientations. Measuring specimen parameters with a deeper, more diverse data set also reduces correlations among parameters and improves measurement accuracy.

As illustrated in FIG. 1, metrology tool 100 includes a specimen positioning system 140 configured to both align specimen 101 and orient specimen 101 over a large range of out of plane angular orientations with respect to the small angle x-ray scatterometer. In other words, specimen positioning system 140 is configured to rotate specimen 101 over a large angular range about one or more axes of rotation aligned in-plane with the surface of specimen 101, resulting in a large range of angles of incidence and azimuth angles of beam incidence relative to the surface of specimen 101. In some embodiments, specimen positioning system 140 is configured to rotate specimen 101 within a range of at least 90 degrees about one or more axes of rotation aligned in-plane with the surface of specimen 101. In some embodiments, specimen positioning system is configured to rotate specimen 101 within a range of at least 60 degrees about one or more axes of rotation aligned in-plane with the surface of specimen 101. In this manner, angle resolved measurements of specimen 101 are collected by metrology system 100 over any number of locations on the surface of specimen 101. In one example, computing system 130 communicates command signals 137 to motion controller 145 of specimen positioning system 140 that indicate the desired position of specimen 101. In response, motion controller 145 generates command signals to the various actuators of specimen positioning system 140 to achieve the desired positioning of specimen 101.

By way of non-limiting example, as illustrated in FIG. 1, specimen positioning system 140 includes an edge grip chuck 141 to fixedly attach specimen 101 to specimen positioning system 140. A rotational actuator 142 is configured to rotate edge grip chuck 141 and the attached specimen 101 with respect to a perimeter frame 143. In the depicted embodiment, rotational actuator 142 is configured to rotate specimen 101 about the x-axis of the coordinate system 146 illustrated in FIG. 1. As depicted in FIG. 1, a rotation of specimen 101 about the z-axis is an in plane rotation of specimen 101. Rotations about the x-axis and the y-axis (not shown) are out of plane rotations of specimen 101 that effectively tilt the surface of the specimen with respect to the metrology elements of metrology system 100. Although it is not illustrated, a second rotational actuator is configured to rotate specimen 101 about the y-axis. A linear actuator 144 is configured to translate perimeter frame 143 in the x-direction. Another linear actuator (not shown) is configured to translate perimeter frame 143 in the y-direction. In this manner, every location on the surface of specimen 101 is available for measurement over a range of out of plane angular positions. For example, in one embodiment, a location of specimen 101 is measured over any number of angular increments within a range of −45 degrees to +45 degrees with respect to the normal orientation of specimen 101.

The large, out of plane, angular positioning capability of specimen positioning system 140 expands measurement sensitivity and reduces correlations between parameters. For example, in a normal orientation, SAXS is able to resolve the critical dimension of a feature, but is largely insensitive to sidewall angle and height of a feature. However, by collecting measurement data over a broad range of out of plane angular positions, the sidewall angle and height of a feature can be resolved.

It should be recognized that the various steps described throughout the present disclosure may be carried out by a single computer system 130 or, alternatively, a multiple computer system 130. Moreover, different subsystems of the system 100, such as the specimen positioning system 140, may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the x-ray detector 116 and the x-ray illumination optics 115 in any manner known in the art. For example, the one or more computing systems 130 may be coupled to computing systems associated with the x-ray detector 116 and the x-ray illumination optics 115, respectively. In another example, any of the x-ray detector 116 and the x-ray illumination optics 115 may be controlled directly by a single computer system coupled to computer system 130.

The computer system 130 of metrology system 100 may be configured to receive and/or acquire data or information from the subsystems of the system (e.g., x-ray detector 116, x-ray illumination optics 115, and the like) by a transmission medium that may include wireline and/or wireless portions. In this manner, the transmission medium may serve as a data link between the computer system 130 and other subsystems of the system 100.

Computer system 130 of the metrology system 100 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 100, external memory 180, or external systems). For example, the computing system 130 may be configured to receive measurement data (e.g., signals 126) from a storage medium (i.e., memory 132 or memory 180) via a data link. For instance, spectral results obtained using a spectrometer of x-ray detector 116 may be stored in a permanent or semi-permanent memory device (e.g., memory 132 or memory 180). In this regard, the spectral results may be imported from on-board memory or from an external memory system. Moreover, the computer system 130 may send data to other systems via a transmission medium. For instance, specimen parameter values 170 determined by computer system 130 may be stored in a permanent or semi-permanent memory device (e.g., memory 180). In this regard, measurement results may be exported to another system.

As described with reference to FIG. 1, metrology system 100 includes a SAXS system. However, in general, measurement recipe refinement based on any suitable x-ray metrology technique, or combination of different optical metrology techniques and different x-ray based metrology techniques may be contemplated within the scope of this patent document. Furthermore, measurements based on any x-ray metrology technique participating in measurement recipe refinement as described herein may be performed on one or more individual metrology tools, one or more combined metrology tools, or any combination thereof without limitation.

By way of non-limiting example, any of the following x-ray metrology techniques including, transmission small angle x-ray scattering (TSAXS), grazing incidence small angle x-ray scattering (GISAXS), wide angle x-ray scattering (WAXS), x-ray reflectivity (XRR), x-ray diffraction (XRD), grazing incidence x-ray diffraction (GIXRD), high resolution x-ray diffraction (HRXRD), x-ray photoelectron spectroscopy (XPS), x-ray fluorescence (XRF), grazing incidence x-ray fluorescence (GIXRF), x-ray tomography, and x-ray ellipsometry may be contemplated within the scope of this patent document.

X-ray metrology techniques applied as described herein may be used to determine characteristics of semiconductor structures. Exemplary structures include, but are not limited to, FinFETs, low-dimensional structures such as nanowires or graphene, sub 10 nm structures, thin films, lithographic structures, through silicon vias (TSVs), memory structures such as DRAM, DRAM 4F2, FLASH and high aspect ratio memory structures. Exemplary structural characteristics include, but are not limited to, geometric parameters such as line edge roughness, line width roughness, pore size, pore density, side wall angle, profile, film thickness, critical dimension, pitch, overlay, and material parameters such as electron density, crystalline grain structure, morphology, orientation, stoichiometry, stress, and strain.

In a further embodiment, metrology system 100 includes one or more computing systems 130 employed to generate a refined a set of values of one or more machine parameters that specify a measurement scenario in accordance with the methods described herein.

Figure 2:
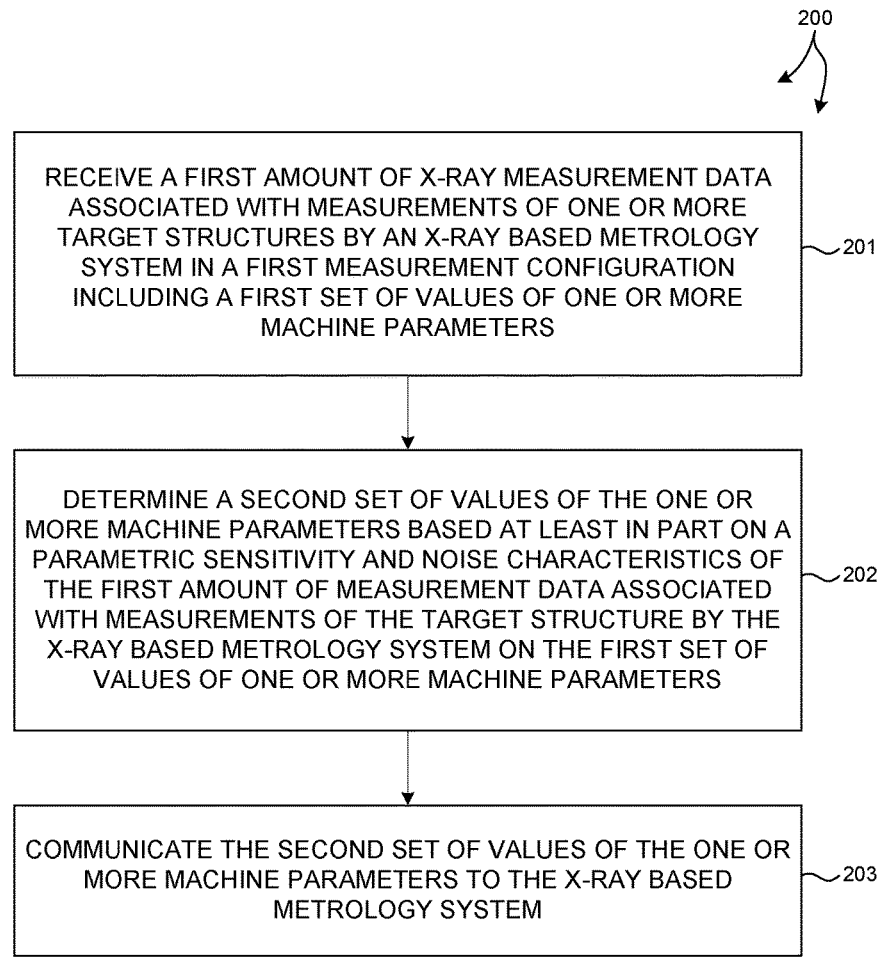
FIG. 2 is a flowchart illustrative of an exemplary method 200 of optimizing a measurement recipe based on refinement of machine parameter values that specify a measurement scenario.

FIG. 2 illustrates a method 200 suitable for implementation by the metrology system 100 of the present invention. In one aspect, it is recognized that data processing blocks of method 200 may be carried out via a pre-programmed algorithm executed by one or more processors of computing system 130. While the following description is presented in the context of metrology system 100, it is recognized herein that the particular structural aspects of metrology system 100 do not represent limitations and should be interpreted as illustrative only.

In block 201, a first amount of x-ray measurement data associated with measurements of one or more target structures is received by computing system 130. In one embodiment, the one or more computing systems 130 are communicatively coupled to the x-ray detector 116. The one or more computing systems 130 are configured to receive measurement data 126 associated with measurements of one or more measurement targets of specimen 102. The measurement data is collected while x-ray based metrology system 100 is in a first measurement configuration including a first set of values of one or more machine parameters.

In block 202, computing system 130 determines a second set of values of the one or more machine parameters, and thus refines the set of values of the machine parameters that specify the measurement scenario (i.e., measurement recipe). The refinement of the values of the one or more machine parameters is based at least in part on a sensitivity of the previous amount of measurement data on the first set of values of one or more machine parameters.

In some examples, the determining of the second set of values of the one or more machine parameters involves determining a measurement model of the one or more target structures. The measurement model relates values of one or more parameters of interest and the previous set of values of the one or more machine parameters to the amount of x-ray measurement data. In some examples, the second set of values of the one or more machine parameters is determined based on an optimization that involves a minimization of a variance or covariance of the values of the one or more parameters of interest subject to a constraint, for example, on measurement duration. In some other examples, the second set of values of the one or more machine parameters is determined based on an optimization that involves a minimization of measurement duration subject to a constraint, for example, on a variance or covariance of the values of the one or more parameters of interest.

In some examples, the machine parameters for which computing system 130 determines a refined set of values includes angle of incidence, azimuth angle, and measurement duration $(\theta,\varphi,\tau)$. For T-SAXS, T-WAXS, or XRD, one or more metrology targets are illuminated at multiple, different angles of incidence, azimuth angles, and measurement durations. The intensity of the diffracted orders is recorded at each angle.

Typically, for gratings that are periodic in one dimension, the target is rotated over a fixed set of evenly-spaced angles orthogonal to direction of periodicity. For gratings that are periodic in two dimensions, the target is rotated over a fixed set of evenly-spaced angles orthogonal to one direction of periodicity and then rotated over a fixed set of evenly-spaced angles orthogonal to the second direction of periodicity. Each angle is measured for the same amount of time.

However, in this example, computing system 130 determines a different set of angles and measurement durations to better realize the measurement objective. In some examples, computing system 130 determines a different set of angles and measurement durations to improve measurement precision. In some examples, computing system 130 determines a different set of angles and measurement durations to minimize correlation among various parameters of interest. In some examples, computing system 130 determines a different set of angles and measurement durations to maximize the accuracy of the measurement.

The optimal set of machine parameters $(\theta,\varphi,\tau)$ is a function of the selected parameter of interest or combination of parameters of interest. The parameter(s) of interest not only affects the values of the optimal set of machine parameters, but also the strategies for initializing the algorithms to find an optimal set. For example, if a precise measurement of sidewall angle is desired, it is known that the angle of incidence with the greatest intensity is at the sidewall angle and its highest sensitivity is nearby. This suggests that an optimal set of machine parameter values $(\theta,\varphi,\tau)$ will include a dense sample of angles of incidence that are chosen from a neighborhood about the sidewall angle.

A practical means of initializing an optimization algorithm would be to choose angles of incidence that span the expected range of the sidewall angle as an initial set. Subsequent refinement would involve selecting additional angles of incidence to optimize the measurement precision of sidewall angle.

In another example, it is desired to de-correlate the measurement of an overlay parameter of interest from other parameters. In this manner, variations in the other parameters have minimal effect on the estimation of the overlay parameter value. In one example, two lines are measured. The target is rotated about an axis parallel to the lines (e.g., $\varphi=0$). The two lines are separated vertically by a height parameter and horizontally by an overlay parameter. It is known that the height and overlay parameters can be de-correlated when a measurement data set includes data collected at every angle, $\theta$, and its opposite, $-\theta$.

In a further aspect, the determined set of machine parameter values is employed in subsequent set of measurements. The resulting measurement data is analyzed again to further optimize the set of values of the machine parameters. Thus, the refinement of the set of values of the machine parameters can be iterated until a desired measurement precision is achieved.

In one example, measurement data is collected using a fixed set of angles of incidence, azimuth angles, and measurement duration. An initial estimate of the values of the parameters of interest is computed. In real time, additional angles of incidence, azimuth angles, and measurement duration $(\theta,\varphi,\tau)$ are computed to maximize the measurement precision of the parameters of interest. Subsequently, measurement data is collected using the additional angles of incidence, azimuth angles, and measurement duration. Improved estimates of the values of the parameters of interest are computed. This process may be conducted iteratively. At each step an increase in measurement precision is maximized.

In some examples, an iterative approach is implemented with multi-target regression data. In one example, the measurement angle set for one target is optimized from measurement results from a previous target. In another example, the angle sets associated with measurements of multiple targets are jointly optimized. In some of these examples, the angle set for one target is different from another target depending on what parameters are being floated jointly or independently.

In another further aspect, determining values of one or more machine parameters involves determining a model that relates values of the one or more machine parameters to the measurement data. A refined set of machine parameter values is determined such that one or more signals of subsequently collected measurement data converges toward a minimum or maximum value. In this manner, changes to values of the machine parameters are driven by values of measured data in an iterative, feedback approach.

In some examples, measurements of the intensities of the diffracted signal are measured for a fixed time period. From the set of fixed time measurements up to the present, values the machine parameters $(\theta,\varphi)$ are determined for the next fixed time period. The refinement of the set of machine parameter values is determined so that the machine parameters $(\theta,\varphi)$ converge to a fixed point or a fixed periodic orbit. From that fixed point (or orbit) in angular space, the desired estimate of the parameter of interest is computed.

In one example, a simple rectangular structure is measured. There is a simple relationship between the height of the structure and the minimum of a scattered signal as a function of measurement angle. The minimum is related to the zero of the sine cardinal function describing the Fourier transform of the rectangular shape. A refinement of the set of machine parameter values is derived to directly control the angle of incidence of the illumination beam of the T-SAXS system depicted in FIG. 1. After the angle of incidence reaches an asymptotic value, an estimate of the height of the structure is made.

In another example, the scattered intensity of the diffracted orders is maximized at the exact overlay angle. A signal indicative of the refined set of machine parameter values is communicated to the T-SAXS mechanism to control the angle of incidence of the illumination beam. After the angle of incidence reaches an asymptotic value, an estimate of overlay is calculated.

A similar approach may be employed with GI-SAXS. However, rather than having the freedom to vary up to two beam angles (θ,φ), a GI-SAXS application generally limits the extent to which varying the incidence angle (θ) is possible.

In general, the signal indicative of the refined set of machine parameter values takes into account the stochastics or statistical properties of the measurement process. In some embodiments, the refinement of the set of machine parameter values is determined by a Kalman filter, Extended Kalman Filter, or any related statistical filter such as a Bayesian or particle filter.

In block 203, computing system 130 communicates the second set of values of the one or more machine parameters to the x-ray based metrology system. In one embodiment, computing system 130 communicates the refined measurement recipe to the appropriate elements of metrology system 100 (e.g., x-ray illumination system 110, specimen positioning system 140, detector 116, etc.).

In a further aspect, measurement data associated with measurements of one or more target structures is simulated. In some examples, a number of simulations of a measurement model, including expected variations in the values of parameters of interest and a noise model, provide measurement data for initialization or refinement of a set of machine parameter values. In one example, measurements of an ensemble of shapes sampled from its expected range are simulated. Additionally, a large set of measurement sensitivities for machine parameters (θ,φ,τ) are computed for each model. A Monte Carlo based algorithm is employed to subsample the set of possible measurement parameters (θ,φ, τ) and select the sample which optimizes an appropriate measure of the desired measurement precision.

In some examples, an estimate of measurement precision of a parameter of interest is computed based on an estimate of measurement noise and the sensitivity of the measurement to changes in value of the parameter of interest. If the measurement noise is presumed to be dominated by shot noise, the estimate of measurement precision may be computed from simulated measurement data and parametric sensitivity alone.

In addition, in some embodiments, the one or more computing systems 130 are further configured to receive a set of reference measurement data 121 associated with a measurement of the specimen 102 by a reference measurement source 122. In some examples, the reference measurement data 121 is stored in memory (e.g., memory 132) and retrieved by computing system 130. In some embodiments, a reference measurement source 122 is another metrology tool capable of highly accurate measurements of a target structure (e.g., TEM, SEM, X-Ray scatterometer, etc.).

The results of the measurement analysis (e.g., specimen parameter values 170) are compared with reference measurement results to determine if a difference between the estimated parameter values and the parameter values derived from the reference measurement is within a predetermined threshold. If so, an optimized measurement recipe based on the refined set of machine parameter values is achieved. If not, the optimization of the set of machine parameter values is iterated until an optimized measurement recipe is achieved.

In general, any number of machine parameters may be refined to improve measurement precision. In some examples, a semiconductor specimen may have large repeating structures which can be measured using a relatively large x-ray spot size (>50 μm) compared to traditional semiconductor metrology. In these examples the size of an opening of x-ray slits 120 or the shape of an x-ray aperture of x-ray optics 115 is adjusted to improve the signal to noise ratio of the measurement. In one embodiment, computing system 130 determines a refined value of the opening of illumination slit 120 based on any of the machine parameter refinement methods described herein, and communicates a command signal 136 to illumination slit 120 to adjust to the desired opening.

In a similar manner, the specimen to detector distance can be optimized for particular samples. Specimen with large pitch structures will produce scattering with small scattering vectors. To resolve these orders, the specimen to detector distance can be increased, for example, by moving the specimen closer to the x-ray source (and hence father from the detector), by moving the detector farther from the specimen and the x-ray source, or a combination of both. In this manner the scattered orders can be resolved on the finite size pixels of the detector. Alternatively, specimen having very small pitch structures exhibit large scattering with very large scattering vectors. In these examples, the detector pixels could be binned without losing resolution. In this way the measurement time can be reduced by reducing the readout time of the collected images. In one embodiment, computing system 130 determines a refined value of the specimen to detector distance based on any of the machine parameter refinement methods described herein, and communicates a command signal to an actuator system (not shown) to adjust to the desired distance.

In another example, the detector location relative to the specimen is optimized. All x-ray detectors have a finite pixel size and a finite number of pixels corresponding to the size of the detector. Often, the detector is placed so that the positive as well as the negative scattering orders are incident upon the detector. However, in some examples the measurement can be optimized by collecting very high order number scattering peaks to capture very high spatial frequency information about the specimen. In this example, the detector is locate relative to the specimen such that only one side of the scattering orders are collected. This will enables more of the higher scattering orders to be incident on the detector. In one embodiment, computing system 130 determines a refined value of the detector location relative to the specimen based on any of the machine parameter refinement methods described herein, and communicates a command signal to an actuator system (not shown) to adjust to the desired location.

In another example, the energy of the x-ray beam is optimized to improve measurement precision. For transmission SAXS measurements the x-ray beam needs to be energetic enough to have a high transmission through the silicon wafer. For conventional x-ray sources this limits the energies to materials such as Molybdenum (~17.5 keV) and Indium (24.2 keV). For grazing incidence measurements lower energy beams such as copper (8 keV) may be more desirable as these sources have a higher brilliance due to material properties of the metal anode. For x-ray sources which are tunable, such as synchrotron sources and Inverse-Compton sources the energies can be tuned to specific absorption edges. This increases the scattering contrast between materials in a technique call resonant-SAXS. In one embodiment, computing system 130 determines a refined value of the beam energy based on any of the machine parameter refinement methods described herein, and communicates a command signal to x-ray illumination system 110 to adjust to the desired beam energy.

In another example, the divergence of the x-ray beam is optimized to improve measurement precision. With a large divergence, the spatial variation in the intensity of the diffracted orders can be observed more easily. This variation in intensity may yield information related to the estimation of a parameter of interest, such as overlay or side wall angle. In one embodiment, computing system 130 determines a refined value of the beam divergence of the x-ray illumination beam incident on the specimen under measurement. Furthermore, computing system 130 communicates a command signal to illumination slit 120, x-ray optics 115, or a combination of both to adjust to the desired beam divergence. This may be achieved, for example, by changing the shape of the x-ray optics 115, changing the opening of x-ray slits 120, or a combination of both.

In another further aspect, multiple targets are employed as part of a refinement of the measurement recipe. In some examples, certain parameters, such as material density, stoichiometry, or incident photon flux are not expected to change from measurement site to measurement site. The values of these parameters are held constant in a multiple target refinement of the measurement recipe. When multiple targets are employed, in some examples, certain parameters are floated together and others separately. For example, it may be that the density of a particular oxide does not vary from site to site, while CD does vary from site to site. In this example, CD is floated independently at each site while the density is treated as a common parameter.

In another further aspect, the values of a parameter of interest are constrained or parameterized as part of a refinement of the measurement recipe. For example, if the density of a material is known to be constrained within a range, a constrained optimization is used as part of the refinement of the measurement recipe. In one example, if the density is known to be a function of the radial position on the wafer, this parameter fixed for a given radial location on the wafer. For X-Ray measurements, constraints on material properties are particularly useful, as it is known that that maximum density of a substance occurs when it is purely crystalline, and varies by only a few percent it is amorphous. Thus, a lower and upper bound can be applied to the density of a material. Similarly, stoichiometry may be fixed, or allowed to vary within specific bands.

X-Ray scattering can be thought of as a single scattering event wherein a photon only scatters from an electron once when passing through a thin structure. This assumption applies well to T-SAXS metrology. As a result, scattering from a particular layer in a metrology target is essentially independent of any other layer. The detected intensity fields from each layer add linearly into the resulting scattered field. If the diffraction patterns from two layers are oriented differently, then the superimposed fields from each layer cannot destructively or constructively interfere, and therefore will not affect the diffraction pattern. An example of this is a Grating-over-Grating or Crossed Grating target, where direction of periodicity of one layer is different from the other. In these examples, the measurement data from the two gratings can be independently analyzed, with the parameters of the top grating fixed for analysis of the bottom grating diffraction pattern, and vice versa. Because fewer parameters are floated for each set of data, the achievable measurement precision is greater than if the parameters were floated jointly.

In another example, the pitch of one layer is different from a pitch of a second layer. If the diffraction pattern from one layer does not overlap with the second, the parameters from the layers are floated independently. If there is partial overlap in the diffracted orders, then parameters associated with those diffracted orders which do not overlap are floated independently and fed forward (fixed) in an optimization using data from diffracted orders that do overlap. This approach is also applicable to GI-SAXS.

In a further embodiment, the one or more computing systems 130 are configured to access model parameters in real-time, employing Real Time Critical Dimensioning (RTCD), or it may access libraries of pre-computed models for determining an optimized measurement recipe in accordance with the methods described herein.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 1, program instructions 134 stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

In some embodiments, a combined x-ray and optical analysis as described herein is implemented as part of a fabrication process tool. Examples of fabrication process tools include, but are not limited to, lithographic exposure tools, film deposition tools, implant tools, and etch tools. In this manner, the results of a combined x-ray and optical analysis are used to control a fabrication process. In one example, x-ray and optical measurement data collected from one or more targets is sent to a fabrication process tool. The x-ray and optical measurement data is analyzed as described herein and the results used to adjust the operation of the fabrication process tool.

In general, the systems and methods described herein can be implemented as part of the process of preparing an optimized measurement recipe for off-line or on-tool measurement. In addition, measurement models may describe one or more target structures.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method comprising:
   providing a first amount of x-ray radiation to one or more target structures on a surface of a semiconductor wafer from an x-ray illumination source of an x-ray based metrology system;
   detecting an amount of radiation from each of the one or more target structures in response to the first amount of x-ray radiation on a detector of the x-ray based metrology system;
   generating a first amount of x-ray measurement data based on the detected amount of x-ray radiation, wherein the first amount of x-ray measurement data is associated with measurements performed by the x-ray based metrology system in a first measurement configuration characterized by a first set of values of one or more machine parameters;
   determining a second set of values of the one or more machine parameters based at least in part on a parametric sensitivity and noise characteristics of the first amount of measurement data associated with the measurements of the one or more target structures by the x-ray based metrology system at the first set of values of the one or more machine parameters; and communicating the second set of values of the one or more machine parameters to the x-ray based metrology system: and
   adjusting the x-ray based metrology system from the first measurement configuration to a second measurement configuration based on the second set of values of the one or more machine parameters;
   wherein rotational and linear actuators are configured to measure a location of one or more targets over any number of angular increments with respect to a normal orientation of the one or more targets.

2. The method of claim 1, further comprising:
   receiving a second amount of x-ray measurement data associated with measurements of the one or more target structures by the x-ray based metrology system in the second measurement configuration including the second set of values of the one or more machine parameters;
   determining a third set of values of the one or more machine parameters based at least in part on a sensitivity of the second amount of measurement data associated with measurements of the target structure by the x-ray based metrology system on the second set of values of one or more machine parameters; and communicating the third set of values of the one or more machine parameters to the x-ray based metrology system.

3. The method of claim 1, further comprising:
determining a measurement model of the one or more target structures that relates values of one or more parameters of interest and the first set of values of the one or more machine parameters to the first amount of x-ray measurement data;
performing a regression of the first amount of measurement data on the measurement model to determine estimated values of the one or more parameters of interest;
receiving an indication of reference values of the one or more parameters of interest;
determining a difference between the estimated values of the one or more parameter values and the reference values of the one or more parameters of interest exceeds a threshold value; and
storing the first set of values of the one or more machine parameters in a memory if the difference between the estimated values of the one or more parameter values and the reference values of the one or more parameters of interest does not exceed a predetermined threshold value.

4. The method of claim 1, wherein the first set of parameters includes at least one of an angle of incidence, an azimuth angle, a beam photon energy, a measurement duration, a beam divergence, an illumination spot size, and a detector location.

5. The method of claim 1, wherein the determining of the second set of values of the one or more machine parameters involves:
determining a measurement model of the one or more target structures that relates values of one or more parameters of interest and the first set of values of the one or more machine parameters to the first amount of x-ray measurement data; and
determining the second set of values of the one or more machine parameters based on an optimization that involves a minimization of a statistical measure of the values of the one or more parameters of interest subject to a constraint on measurement duration.

6. The method of claim 5, wherein the statistical measure is indicative of the variance or covariance of the values of the one or more parameters of interest.

7. The method of claim 2, wherein the determining of the second set of values of the one or more machine parameters involves:
determining a model that relates the first set of values of the one or more machine parameters to the first amount of measurement data; and
determining the second set of values of the one or more machine parameters such that one or more signals of the second amount of measurement data converges toward a minimum or maximum value.

8. The method of claim 7, wherein the model that relates the first set of values of the one or more machine parameters to the first amount of measurement data is a stoichastic filter.

9. The method of claim 1, wherein the first amount of x-ray measurement data associated with measurements of the one or more target structures by the x-ray based metrology system is generated by simulation.

10. The method of claim 5, further comprising:
reducing a number of floating parameters of the measurement model of the one or more target structures that relates values of the one or more parameters of interest and the first set of values of the one or more machine parameters to the first amount of x-ray measurement data.

11. The method of claim 10, wherein the reducing the number of floating parameters involves any of a constraint equation defining a relationship between two or more parameters, a correlation matrix defining the relationship between two or more parameters, and a set of expected profiles selected by a user.

12. An x-ray based metrology system, comprising:
an x-ray illumination source providing x-ray illumination incident onto a specimen under measurement;
an x-ray detector collecting an amount of x-ray radiation diffracted or scattered from the specimen in response to the incident x-ray illumination; and a computing system configured to:
receive a first amount of x-ray measurement data associated with measurements of one or more target structures on the specimen by the x-ray based metrology system in a first measurement configuration characterized by a first set of values of one or more machine parameters;
determine a second set of values of the one or more machine parameters based at least in part on a parametric sensitivity and noise characteristics of the first amount of measurement data associated with measurements of the target structure by the x-ray based metrology system on the first set of values of one or more machine parameters: and
communicate the second set of values of the one or more machine parameters to the x-ray based metrology system, wherein the x-ray based metrology system adjusts from the first measurement configuration to a second measurement configuration based on the second set of values of the one or more machine parameters;
wherein rotational and linear actuators are configured to measure a location of the specimen over any number of angular increments with respect to a normal orientation of the specimen.

13. The x-ray based metrology system of claim 12, wherein the computing system is further configured to:
receive a second amount of x-ray measurement data associated with measurements of the one or more target structures by the x-ray based metrology system in a second measurement configuration including the second set of values of the one or more machine parameters; and
determine a third set of values of the one or more machine parameters based at least in part on a sensitivity of the second amount of measurement data associated with measurements of the target structure by the x-ray based metrology system on the second set of values of one or more machine parameters.

14. The x-ray based metrology system of claim 12, wherein the computing system is further configured to:
determine a measurement model of the one or more target structures that relates values of one or more parameters of interest and the first set of values of the one or more machine parameters to the first amount of x-ray measurement data;
perform a regession of the first amount of measurement data on the measurement model to determine estimated values of the one or more parameters of interest;
receive an indication of reference values of the one or more parameters of interest;
determine a difference between the estimated values of the one or more parameter values and the reference values of the one or more parameters of interest exceeds a threshold value; and store the first set of values of the one or more machine parameters in a memory if the difference between the estimated values of the one or more parameter values and the reference values of the one or more parameters of interest does not exceed a predetermined threshold value.

15. The x-ray based metrology system of claim 12, wherein the determining of the second set of values of the one or more machine parameters involves:

determining a measurement model of the one or more target structures that relates values of one or more parameters of interest and the first set of values of the one or more machine parameters to the first amount of x-ray measurement data; and determining the second set of values of the one or more machine parameters based on an optimization that involves a minimization of a statistical measure indicative of the variance or covariance of the values of the one or more parameters of interest subject to a constraint on measurement duration.

16. The x-ray based metrology system of claim 13, wherein the determining of the second set of values of the one or more machine parameters involves:

determining a model that relates the first set of values of the one or more machine parameters to the first amount of measurement data; and determining the second set of values of the one or more machine parameters such that one or more signals of the second amount of measurement data converges toward a minimum or maximum value.

17. An x-ray based metrology system, comprising:

an x-ray illumination source providing x-ray illumination incident onto a specimen under measurement;

an x-ray detector collecting an amount of x-ray radiation diffracted or scattered from the specimen in response to the incident x-ray illumination; and a non-transitory, computer-readable medium, comprising: code for causing a computer system to:

receive a first amount of x-ray measurement data associated with measurements of one or more target structures by an x-ray based metrology system in a first measurement configuration characterized by a first set of values of one or more machine parameters;

determine a second set of values of the one or more machine parameters based at least in part on a parametric sensitivity and noise characteristics of the first amount of measurement data associated with measurements of the target structure by the x-ray based metrology system on the first set of values of one or more machine parameters;

communicate the second set of values of the one or more machine parameters to the x-ray based metrology system; and adjust the x-ray based metrology system from the first measurement configuration to a second measurement configuration based on the second set of values of the one or more machine parameters;

wherein rotational and linear actuators are configured to measure a location of the specimen over any number of angular increments with respect to a normal orientation of the specimen.

18. The x-ray based metrology system of claim 17, the non-transitory, computer-readable medium, further comprising code for causing the computer to:

receive a second amount of x-ray measurement data associated with measurements of the one or more target structures by the x-ray based metrology system in a second measurement configuration including the second set of values of the one or more machine parameters; and determine a third set of values of the one or more machine parameters based at least in part on a sensitivity of the second amount of measurement data associated with measurements of the target structure by the x-ray based metrology system on the second set of values of one or more machine parameters.

19. The x-ray based metrology system of claim 17, the non-transitory, computer-readable medium, further comprising code for causing the computer to:

determine a measurement model of the one or more target structures that relates values of one or more parameters of interest and the first set of values of the one or more machine parameters to the first amount of x-ray measurement data;

perform a regression of the first amount of measurement data on the measurement model to determine estimated values of the one or more parameters of interest;

receive an indication of reference values of the one or ef-more parameters of interest;

determine a difference between the estimated values of the one or more parameter values and the reference values of the one or more parameters of interest exceeds a threshold value; and store the first set of values of the one or more machine parameters in a memory if the difference between the estimated values of the one or more parameter values and the reference values of the one or more parameters of interest does not exceed a predetermined threshold value.

20. The x-ray based metrology system of claim 18, wherein the determining of the second set of values of the one or more machine parameters involves:

determining a measurement model of the one or more target structures that relates values of one or more parameters of interest and the first set of values of the one or more machine parameters to the first amount of x-ray measurement data; and determining the second set of values of the one or more machine parameters based on an optimization that involves a minimization of a statistical measure indicative of the variance or covariance of the values of the one or more parameters of interest subject to a constraint on measurement duration.

* * * * *